(12) United States Patent
Ban et al.

(10) Patent No.: US 8,541,561 B2
(45) Date of Patent: Sep. 24, 2013

(54) DNA APTAMER SPECIFICALLY BINDING TO pLDH (PLASMODIUM LACTATE DEHYDROGENASE)

(75) Inventors: Changill Ban, Pohang-si (KR); Weejeong Jeon, Daejeon (KR); Seonghwan Lee, Uijeongbu-si (KR)

(73) Assignee: Postech Academy-Industry Foundation, Pohang-Si, Gyeongsangbuk-Do (KR)

( * ) Notice: Subject to any disclaimer, the term of this patent is extended or adjusted under 35 U.S.C. 154(b) by 0 days.

(21) Appl. No.: 13/355,159

(22) Filed: Jan. 20, 2012

(65) Prior Publication Data

US 2012/0316325 A1 Dec. 13, 2012

(30) Foreign Application Priority Data

Jun. 7, 2011 (KR) ........................ 10-2011-0054796

(51) Int. Cl.
*C07H 21/04* (2006.01)
*C12Q 1/68* (2006.01)

(52) U.S. Cl.
USPC ........................................ 536/23.1; 435/6.1

(58) Field of Classification Search
None
See application file for complete search history.

(56) References Cited

U.S. PATENT DOCUMENTS

2011/0003886 A1  1/2011  Lindh et al.

FOREIGN PATENT DOCUMENTS

| KR | 10-2004-00235 A | 3/2004 |
| KR | 10-2007-0097648 A | 10/2007 |
| WO | 2009/075404 A1 | 6/2009 |
| WO | 2009/099378 A1 | 8/2009 |

OTHER PUBLICATIONS

Cheung Y W et al: E2-22: New avenues to malaria diagnosis—nucleic acid aptamers against *P-falciparum* histidine rich protein 2 and lactate dehydrogenase:, FEBS Journal; 35th Congress of the Federation-of-European-Biochemical-Societies, Blackwell Publishing, London, GB; Gothenburg, Sweden, vol. 277, No. Suppl. 1, Jun. 1, 2010, pp. 244-245, XP008153614, ISSN: 2853-464X.
Ulrich Henning et al: "In vitro Selection of RNA Aptamers That Bind to Cell Adhesion Receptors of *Trypanosoma cruzi* and Inhibit Cell Invasion", Journal of Biological Chemistry, The American Society of Biological Chemists, Inc, US, vol. 277, No. 23, Jun. 7, 2002 ,pp. 20756-20762, XP003025173, ISSN: 0021-9258.
Anders Barfod et al: "In vitro selection of RNA aptamers against a conserved region of the *Plasmodium falciparum* erythrocyte membrane protein 1", Parasitology Research ; Founded As Zeitschrift Fur Parasitenkunde, Springer, Berlin, DE, vol. 105, No. 6, Aug. 20, 2009, pp. 1557-1566, XP019760646, ISSN: 1432-1995.
Jacquin C. Niles et al: "Inhibiting *Plasmodium falciparum* growth and heme detoxification pathway using heme-binding DNA aptamers", Proc Natl Acad Sci USA., vol. 106, No. 32, Aug. 11, 2009, pp. 13266-13271, XP55035557.
Moody A: "Rapdi diagnostic tests for malaria parasites", Clinical Mocrobiology Reviews, Washington, DE, US, vol. 15, No. 1, Jan. 1, 2002, pp. 66-78, XP003007430, ISSN: 0893-8512.
Goringer H Ulrich et al: "In vitro selection of high-affinity nucleic acid ligands to parasite target molecules", International Journal of Parasitology, Pergamon Press, GB, vol. 33, No. 12, Jan. 1, 2003, pp. 1309-1317, XP003025175, ISSN: 0020-7519.
Seonghwan Lee et al: "A highly sensitive aptasensor towards *Plasmodium lactate* dehydrogenase for the diagnosis of malaria", Biosensors and Bioelectronics, vol. 35, No. 1, May 1, 2012, pp. 291-296, XP55032995, ISSN: 0956-5663.
European Search Report dated Oct. 17, 2012 of corresponding European Patent Application No. 12151425.1—9 pages.
Notice of Allowance dated Jul. 9, 2013 of corresponding Korean Application No. 10-2011-0054796.

*Primary Examiner* — Tracy Vivlemore
(74) *Attorney, Agent, or Firm* — Knobbe, Martens, Olson & Bear, LLP

(57) ABSTRACT

Disclosed herein are a DNA aptamer specifically binding to pLDH (*Plasmodium* Lactate Dehydrogenase), a composition for the diagnosis of malaria, comprising the same, and a diagnostic kit for malaria using the same. Superior in specificity and stability to antibodies which are conventionally used to diagnose malaria, the DNA aptamers specifically binding to pLDH (*Plasmodium* Lactate Dehydrogenase) in accordance with the present invention can be developed into biosensors which determine pLDH levels with high sensitivity and accuracy, greatly contributing to the diagnostic accuracy of malaria.

4 Claims, 8 Drawing Sheets

(a) (b)

Aptamer-protein (PvLDH or PfLDH) complex

Aptamer-protein (PvLDH or PfLDH) complex

FIG. 8

Aptamer# 2 <u>GAACTCA</u>TTGGCTGGAGGCGGCAGTACCGCT<u>TGAGTTC</u> (SEQ ID NO: 2)

Aptamer#1 <u>GTTCGA</u>TTGGATTGTGCCGGAAGTGCTGGC<u>TCGAAC</u> (SEQ ID NO: 1)

mutation

| Loop 1 | GTTCGACCAAATTGTGCCGGAAGTGCTGGCTCGAAC (SEQ ID NO: 3) |
| G-C rich Stem | GTTCGATTGGATTGTACTGAAAGTGTCAGTTCGAAC (SEQ ID NO: 4) |
| Loop 2 | GTTCGATTGGATTGTGCCGGAGACGCTGGCTCGAAC (SEQ ID NO: 5) |

DNA APTAMER SPECIFICALLY BINDING TO PLDH (PLASMODIUM LACTATE DEHYDROGENASE)

CROSS-REFERENCE(S) TO RELATED APPLICATIONS

The present application claims priority of Korean Patent Application No. 10-2011-0054796, filed on Jun. 7, 2011, which is incorporated herein by reference in its entirety.

BACKGROUND OF THE INVENTION

1. Field of the Invention

The present invention relates to a DNA aptamer specifically binding to pLDH (*Plasmodium* Lactate Dehydrogenase) and a composition for the diagnosis of malaria.

2. Description of the Related Art

Symptoms of malaria include headache, myalgia, fever, vomiting, and the like. However, malaria cannot be diagnosed on the basis of these symptoms because they are not unique to malaria. Typically, malaria is confirmed by microscopic examination, which is, however, unsuitable for use in initial diagnosis in malaria prevalent regions because the method requires expensive instruments and skilled operators. An immunochromatographic diagnosis assay provides a potential alternative. Based on antigen-antibody reactions, typical immunochromatographic portable diagnosis kits, however, may vary in diagnostical accuracy depending on the storage environment thereof. An initial countermeasure in response to an initial diagnosis performed in the scene of outbreak of malaria has a great influence on the subsequent treatment of malaria, so that portable diagnosis kits must have high performance.

pLDH is an essential enzyme, detectable in malarial parasites over their entire life, and one that is involved in the metabolism of malarial parasites. All four kinds of malarial parasites have the enzyme in a highly conserved amino acid sequences. Most of the currently available portable malaria diagnostic kits are based on antibodies to pLDH and can be used to diagnose all four types of malaria.

An aptamer is a single strand DNA (ssDNA) or RNA (ssRNA) that binds to a specific target. Thanks to their high affinity and stability to a specific target, they have recently been extensively developed and actively applied to the therapy and sensors for diagnosis of diseases. The synthesis of aptamers can be relatively simply, and cells, proteins and even small organic substance can be utilized as their targets, which allows for the development of new detection methods. In addition, aptamers find a wide range of applications in various fields, including the development of therapeutics, drug delivery systems, biosensors for diagnosis, etc. because they are superior in specificity and stability to the antibodies that were developed previously.

Antibodies developed for diagnostic use are prepared using the immune system and thus suffer from the disadvantage of their preparation consuming comparatively a lot of time and expense. Further, they are proteins that have poor stability, compared to aptamers, DNA or RNA, which may act as an obstruction to the development of highly sensible sensors. In light of the fact that most malaria-prevalent regions are hot and moist, diagnostic systems based on antibodies show low accuracy.

There is therefore a need for a diagnosis system of malaria that can overcome problems encountered in the prior art.

SUMMARY OF THE INVENTION

The present invention is to provide a DNA aptamer specifically binding to pLDH (*Plasmodium* Lactate Dehydrogenase), a composition for the diagnosis of malaria, comprising the same, and a diagnosis kit of malaria using the same.

However, the technical objects to be achieved by the present invention are not limited to those mentioned above and other objects may be clearly understood by those skilled in the art from the description given below.

In accordance with an aspect thereof, the present invention provides an aptamer that specifically binds to pLDH (plasmodium lactate dehydrogenase) which has the base sequence of SEQ ID NO: 1 or 2.

In accordance with another aspect thereof, the present invention provides a composition for the diagnosis of malaria, comprising a DNA aptamer specifically binding to pLDH (*Plasmodium* Lactate Dehydrogenase).

In accordance with a further aspect thereof, the present invention provides a diagnostic kit for malaria that uses a DNA aptamer that specifically binds to pLDH (*Plasmodium* Lactate Dehydrogenase).

In some embodiments of the present invention, the DNA aptamer shares a sequence homology of 70%, 71%, 72%, 73%, 74%, 75%, 76%, 77%, 78%, 79% or higher with the base sequence of SEQ ID NO: 1 or 2. In alternative embodiments, the DNA shares a sequence homology of 80%, 81%, 82%, 83%, 84%, 85%, 86%, 87%, 88%, 89% or higher with the base sequence of SEQ ID NO: 1 or 2. In still alternative embodiments, the DNA aptamer shares a sequence homology of 91%, 92%, 93%, 94%, 95%, 96%, 97%, 98%, 99% or higher with the base sequence of SEQ ID NO: 1 or 2.

Superior in specificity and stability to antibodies which are conventionally used to diagnose malaria, the DNA aptamers specifically binding to pLDH (*Plasmodium* Lactate Dehydrogenase) in accordance with the present invention can be developed into biosensors which determine pLDH levels with high sensitivity and accuracy, greatly contributing to the diagnostic accuracy of malaria.

BRIEF DESCRIPTION OF THE DRAWINGS

The above and other objects, features and other advantages of the present invention will be more clearly understood from the following detailed description taken in conjunction with the accompanying drawings, in which.

Figure 1:
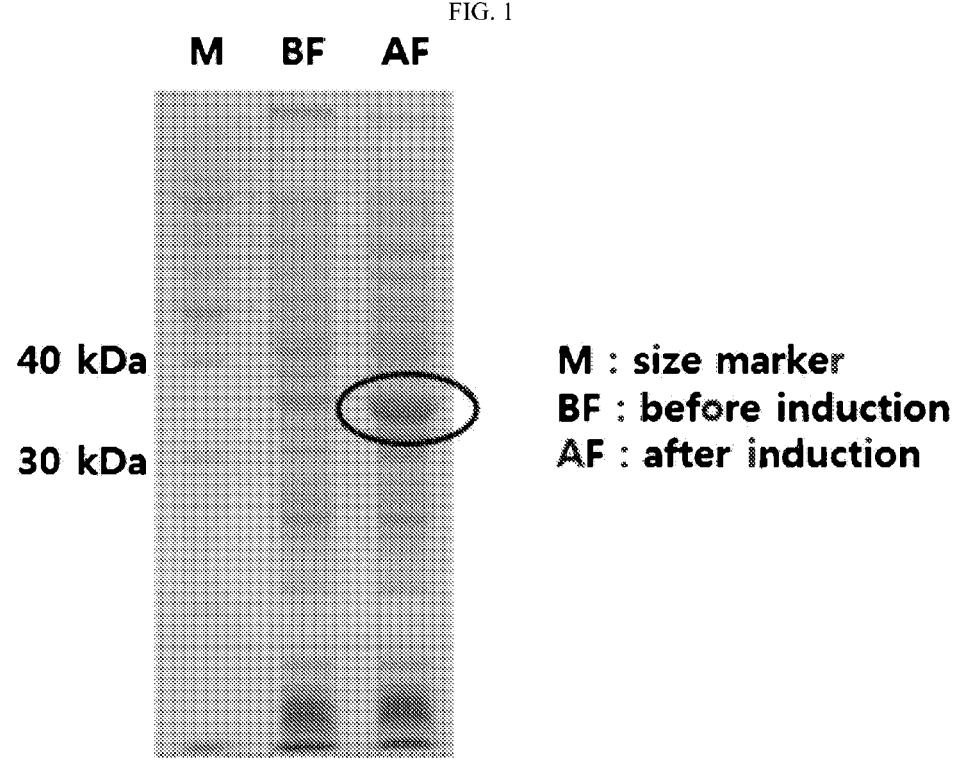
FIG. 1 shows the expression of pvLDH protein as measured by SDS PAGE.
Figure 7:
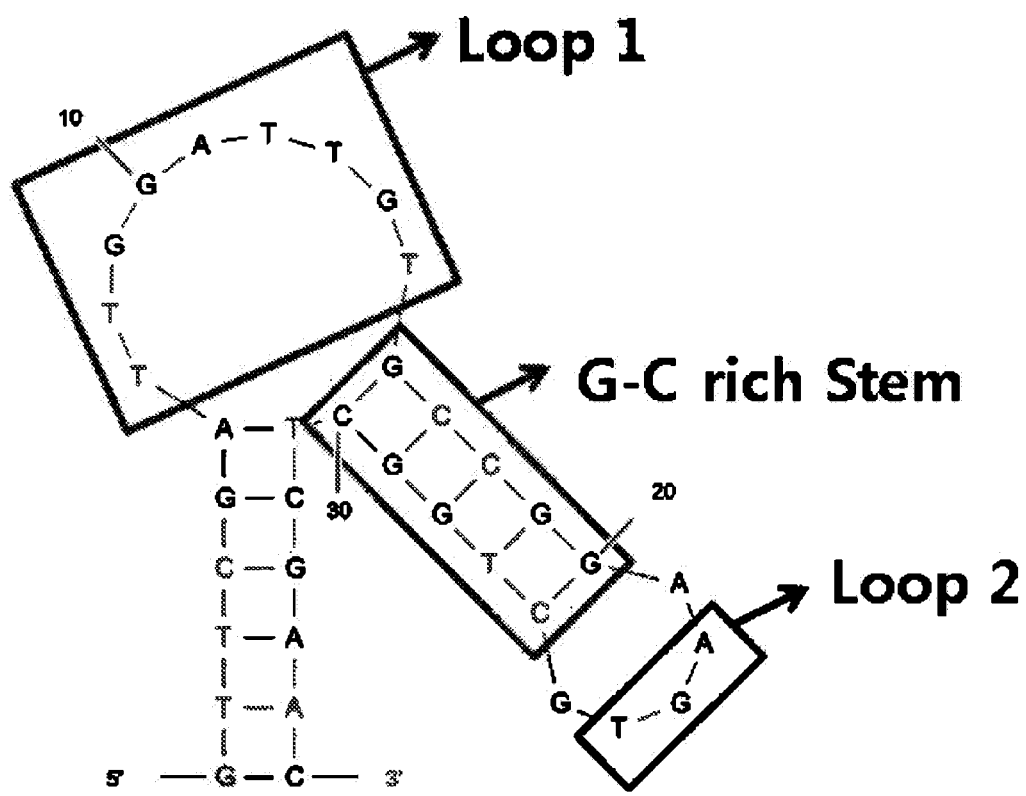
Figure 9:
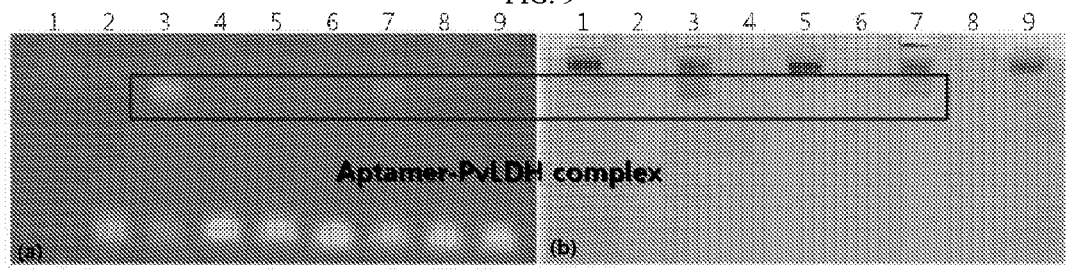

Aptamer #1, lane 5: Aptamer #1+PvLDH, lane 6: PfLDH, lane 7: Aptamer #2, lane 8: Aptamer #2+PfLDH, lane 9: Aptamer #1, lane 10: Aptamer #1+PfLDH);

FIG. 7 shows an expected secondary structure of the aptamer of SEQ ID NO: 1;

FIG. 8 shows base sequences of the aptamer mutants, used in the mutation assay of the Example, wherein mutation bases are marked; and FIG. 9 show the ability of the aptamer mutants as measured by EMSA (Electrophoretic mobility shift assay) (lane 1: pvLDH, lane 2: aptamer #1, lane 3: aptamer #1+pvLDH, lane 4: loop 1 mutant, lane 5: loop 1 mutant+pvLDH, lane 6: stem mutant, lane 7: stem mutant +pvLDH, lane 8: loop 2 mutant, lane 9: loop 2 mutant+pvLDH).

DESCRIPTION OF THE PREFERRED EMBODIMENTS

To develop an aptamer as a substitute for an antibody to pLDH, pLDH was expressed in a bacterial expression system, purified, and utilized to select DNA aptamers with the SELEX (Systematic Evolution of Ligands by EXponential enrichment) technique, which were then analyzed for sequence and structure, culminating in the present invention.

In greater detail, the present invention provides a DNA aptamer having the base sequence of SEQ ID NO: 1 or 2 that specifically binds to pLDH (*plasmodium* lactate dehydrogenase).

Also, the present invention provides a composition for the diagnosis of malaria, comprising a DNA aptamer specifically binding to pLDH (*Plasmodium* Lactate Dehydrogenase).

In addition to the DNA aptamer, the composition of the present invention may comprise pharmaceutically or physiologically acceptable vehicles, excipients or diluents.

Examples of the vehicles, excipients and diluents include lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinylpyrrolidone, water, methyl hydroxybenzoate, propylhydroxybenzoate, talc, magnesium stearate, and mineral oil. When formulated into dosage forms, the composition may further comprise typical filters, thickeners, binders, disintegrants, surfactants, anti-coagulants, lubricants, wetting agents, fragrant, emulsifiers, and/or preservatives.

Also, the present invention provides a diagnostic kit for malaria, using a DNA aptamer specifically binding to pLDH (*Plasmodium* Lactate Dehydrogenase).

Preferably, the DNA aptamer of the present invention has the base sequence of SEQ ID NO: 1 or 2, but is not limited thereto. If it shares a 70% or greater homology with the base sequence of SEQ ID NO: 1 or 2, a DNA aptamer falls within the scope of the present invention. The DNA aptamer according to the present invention has three essential regions: (i) loop 1 (5'-TTCCNTNGN-3'), (ii) G-C rich stem and (iii) loop 2 (5'-AGT-3'). When it has the three regions, any DNA aptamer may be used in the present invention even if the other region thereof may be different from the corresponding region of the base sequence of SEQ ID NO: 1 or 2.

Examples of the pLDH include pvLDH (*plasmodium vivax* lactate dehydrogenase), pfLDH (*plasmodium falciparum* lactate dehydrogenase), pmLDH (*plasmodium malariae* lactate dehydrogenase), and poLDH (*plasmodium ovale* lactate dehydrogenase), but are not limited thereto.

A better understanding of the present invention may be obtained through the following examples which are set forth to illustrate, but are not to be construed as limiting the present invention.

Example 1 pvLDH (*Plasmodium vivax* Lactate Dehydrogenase) Gene Cloning

For use in the amplification of a pvLDH gene, a 5' primer with a BamH1 restriction site (CCCGGATCCATGACGC-CGAAAATTGT; SEQ ID NO: 6) and a 3' primer with a XhoI restriction site (CCCCTCGAGTTAAATGAGCGCCT-TCATCCTTTTAGTCT; SEQ ID NO: 7) were synthesized. Using these primers, amplification was conducted on the genomic DNA of *Plasmodium vivax* in the presence of i-pfu polymerase. PCR was performed with 35 cycles of 1) denaturing the double strand of the template at 94° C. for 30 sec, 2) annealing the template with the primers at 56° C. for 30 sec, and 3) extending new strands at 72° C. for 1 min.

The amplified pvLDH gene was digested with the restriction enzymes, ligated to a pET28a vector containing (His)6-tag and transformed into BL21(DE3) *E. coli*.

Example 2

Expression of pvLDH Protein

The BL21(DE3) cells transformed with the pvLDH gene were grown at 37° C. in an LB (Luria Bertani) medium to an $OD_{600}$ (optical density) of 0.6. Subsequently, the expression of the protein was induced by incubating the cells at 18° C. for 16 hours in the presence of 0.2 mM IPTG (isopropyl-thio-β-D-galactopyranoside). The expression of the protein was confirmed by SDS-PAGE (sodium dodecyl sulfate polyacrylamide gel electrophoresis). After being harvested by centrifugation, the cells were washed once with PBS (10 mM sodium phosphate, 150 mM NaCl, pH 7.4). The SDS-PAGE results are shown in FIG. 1.

Example 3

Purification of pvLDH Protein

To isolate the pvLDH protein expressed in the bacterial cell BL21(DE3) to a high purity, the cells were lysed in a lysis buffer (20 mM Tris, 500 mM NaCl, 0.5 mM β-mercaptoethanol, 5% glycerol, 10 mM imidazole, pH 8.0) and ruptured by sonication for min. Centrifugation at 12,000 rpm for 40 min separated proteins in a supernatant from the cell debris.

The affinity of Ni-NTA for the (His)6-tag amino acid residues was used to isolate the protein to a high purity. In this regard, FPLC (Fast protein liquid chromatography) was coupled with an Ni-NTA column to which the supernatant containing pvLDH was then loaded. The target protein bound to the column was eluted with elution buffer (20 mM Tris, 500 mM NaCl, 0.5 mM β-mercaptoethanol, 5% glycerol, 400 mM imidazole, pH 8.0) because the (His)6-tag of the protein competes with imidazole.

Figure 2:
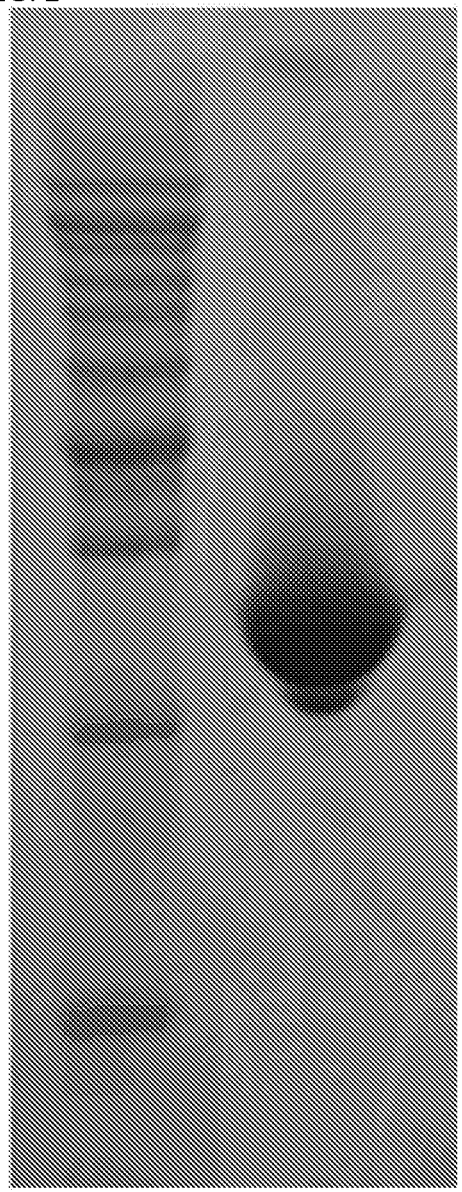
FIG. 2 shows the isolation of pvLDH protein as purified by gel filtration (Superdex200 column)

To obtain more pure protein, the fraction containing pvLDH was allowed to flow through the ion exchange column MonoQ coupled with FPLC to separate proteins according to pI. Because pvLDH is not bound to the column, the non-binding fraction was subjected to size exclusion chromatography by gel filtration using a Superdex200 column. The results are shown in FIG. 2.

Example 4

Search for Aptamers of pvLDH by SELEX

<4-1> Construction of ssDNA (Single-Stranded DNA) Library

A library of 90 sequences, each having primer sequences for PCR amplification and cloning at opposite ends with a random DNA sequence of 40 bases between the primer sequences, was constructed (5'-CACCTAATACGACTCAC-TATAGCGGATCCGA-N40-CTGGCTCGAACAAGCT-TGC-3'; SEQ ID NO: 8).

In addition, a 5' primer (5'-CACCTAATACGACTCAC-TATAGCGGA-3'; SEQ ID NO: 9), a 3' primer (5'-GCAAGCTTGTTCGAGCCAG-3'; SEQ ID NO: 10) and a biotin-conjugated 3' primer (5'-Biotin-GCAAGCTTGTTC-GAGCCAG-3'; SEQ ID NO: 11) were used for PCR amplification and ssDNA production. All the oligonucleotides used in the present invention were synthesized and subjected to PAGE purification by Bionics (Korea).

<4-2> Immobilization of pvLDH to Ni-NTA Magnetic Beads

The purified pvLDH was immobilized to the magnetic bead Dynabead (Invitrogen, Norway), which can allows His-tag to bind to its cobalt-coated surface.

In this regard, the protein was fixed to the beads by washing 20 µL of the beads with a binding buffer (20 mM Tris, 50 mM NaCl, 5 mM KCl, 5 mM $MgCl_2$, pH8.0) by means of an external magnet and incubating the beads with 100 µL of a binding buffer containing 500 pmol of the protein.

<4-3> Selection of Aptamer Specific for pvLDH

To select aptamers specific for pvLDH, a specific separation method using a magnet was conducted.

First, a library of the ssDNAs (1 nmol) was dissolved in 100 µL of a binding buffer and was incubated at 90° C. for 3 min and then at 4° C. for one hour to allow the ssDNA to form the most stable conformation. Subsequently, this library was reacted for one hour with the pvLDH protein immobilized to the magnetic bead, with gentle agitation. Then, the beads were washed twice with the binding buffer to remove the ssDNA which remained unbound to the pvLDH immobilized to the beads.

Afterwards, the ssDNA was separated from the proteins bound thereto. In this context, the ssDNA and the proteins bound thereto were eluted with elution buffer (20 mM Tris, 50 mM NaCl, 5 mM KCl, 5 mM $MgCl_2$, 0.01% tween 20, 300 mM imidazole, pH 8.0). The ssDNA eluate was precipitated in ethanol, dissolved in 60 µL of distilled water, and used as a template for PCR amplification using the 5' primer and the biotin-conjugated 3' primer in the presence of i-pfu polymerase (Intron Biotechnology, Korea). To isolate ssDNA for selection, the biotin-conjugated PCR product was incubated for one hour with streptavidin-coated magnetic beads in a coupling buffer (5 mM Tris-HCl, 0.5 mM EDTA, 1 M NaCl, 0.005% Tween 20, pH 7.5), followed by incubation with 100 µL of 100 mM NaOH for 5 min to separate only ssDNA. The ssDNA was obtained using an external magnet.

Figure 3:
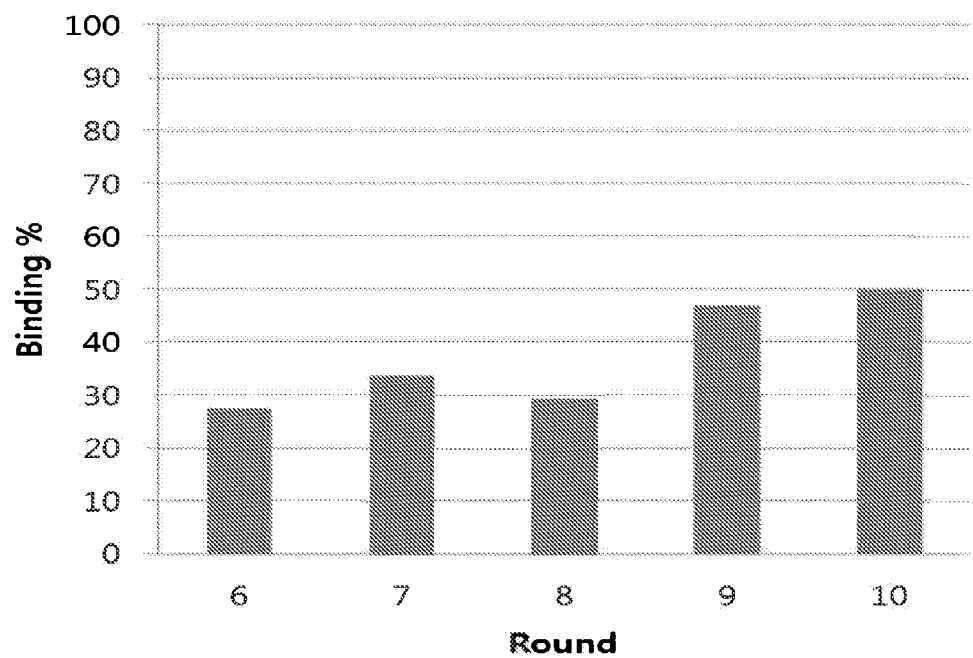
FIG. 3 is a graph showing the binding strength of ssDNA aptamers to pvLDH as measured by a UV spectrometer according to selection of aptamer specific for pvLDH.

The first selected ssDNA was used in subsequent repetitive selection. For stringent selection, the amount of ssDNA and the concentration of pvLDH were gradually decreased in subsequent repetitions. During the selection process, the binding of ssDNA to pvLDH was monitored by measuring the concentration of the ssDNA eluted in repeated selection with a UV spectrometer (Biochrom Libra S22 spectrometer). The results are shown in FIG. 3.

<4-4> Analysis of Sequence and Structure of Aptamers

The ssDNA selected in the $10^{th}$ round was amplified by PCR using the unmodified 5' and 3'primers and cloned to pENTR/TOPO (TOPO TA Cloning kit, Invitrogen, USA) which was then transformed into E. coli TOP10 (Invitrogen, USA). The clones harboring the ssDNA were purified using a miniprep kit (GeneAll, Korea) and subjected to base sequencing (COSMO Genetech, Korea). As a result, the ssDNA sequences were identified as SEQ ID NOS: 1 and 2 and are listed in Table 1, below.

Figure 4:
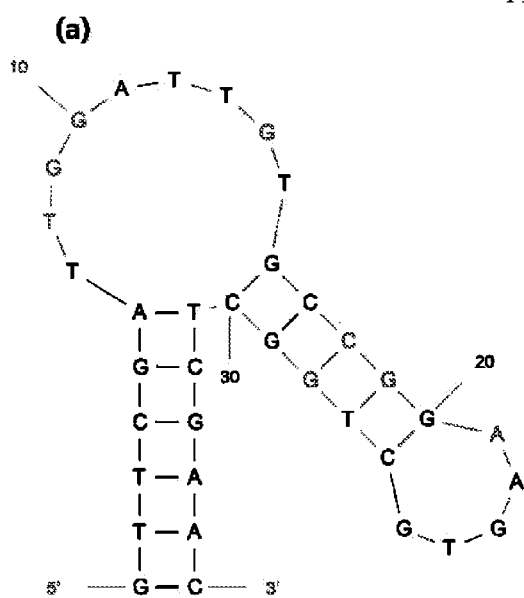
FIG. 4 shows the secondary structures of selected ssDNAs of SEQ ID NOS 1 (a) and 2 (b) as expected by the Mfold program.
Figure 4:
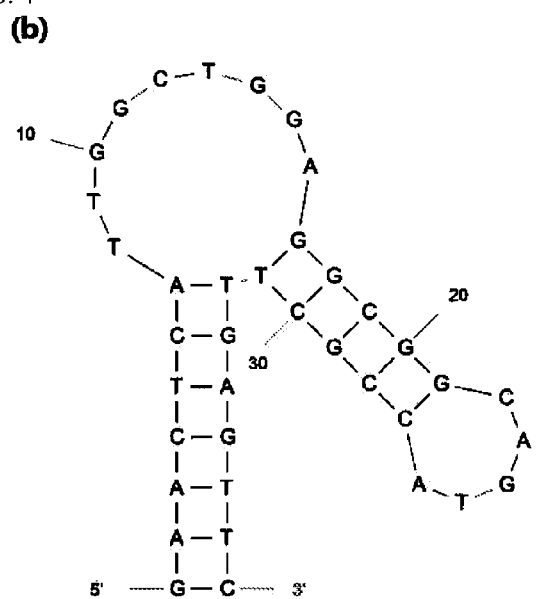
Figure 5:
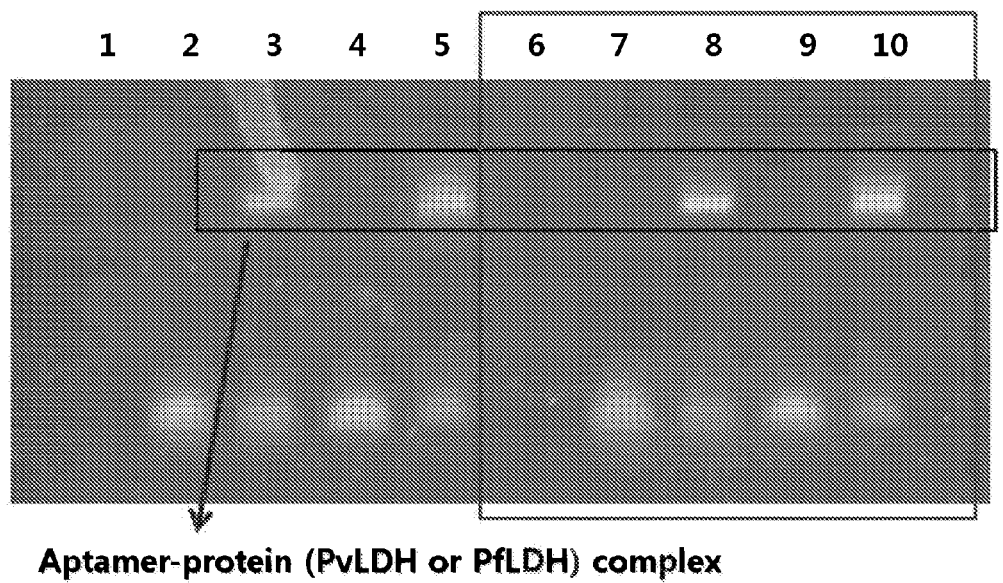
FIG. 5 shows the ability of aptamers of SEQ ID NOS: 1 and 2 to bind to pvLDH (*plasmodium vivax* lactate dehydrogenase) and pfLDH (*plasmodium falciparum* lactate dehydrogenase) as measured by EMSA (Electrophoretic mobility shift assay) (stained with SYBR® green, lane 1: PvLDH, lane 2: Aptamer #2, lane 3: Aptamer #2+PvLDH, lane 4: Aptamer #1, lane 5: Aptamer #1+PvLDH, lane 6: PfLDH, lane 7: Aptamer #2, lane 8: Aptamer #2+PfLDH, lane 9: Aptamer #1, and lane 10: Aptamer #1+PfLDH)

To analyze the structural similarity of the selected ssDNA, the secondary structures of the selected ssDNA sequences were analyzed using the Mfold program operated by Rensselaer Polytechnic Institute which is now the UNAFold. As shown in FIGS. 4 and 5, they were found to have a common sequence and structure.

TABLE 1

| SEQ ID NO: | Base Sequence |
|---|---|
| 1 | GTTCGATTGGATTGTGCCGGAAGTGCTGGCTCGAAC |
| 2 | GAACTCATTGGCTGGAGGCGGCAGTACCGCTTGAGTTC |

Example 5

Electrophoretic Mobility Shift Assay (EMSA) of the Aptamers for Ability to Bind to LDH of Other Species than *Plasmodium vivax*

EMSA (Electrophoretic mobility shift assay) was conducted to examine whether the aptamers of SEQ ID NOS: 1 and 2 can bind to LDH from other malarial parasite species than pvLDH.

In 20 µL of binding buffer, 0.5 µM of each of the aptamers of SEQ ID NOS: 1 and 2 was incubated at room temperature for one hour with 0 µM or 2.5 µM of pvLDH (*plasmodium vivax* lactate dehydrogenase) or pfLDH (*plasmodium falciparum* lactate dehydrogenase), followed by running on 6% acrylamide gel in an electric field of 120 volts for 40 min at a temperature as low as 0° C. so as to prevent the heat-induce denaturation of the protein-aptamer complex. The gel was stained with SYBR® green and coomassie blue and the staining results are shown in FIGS. 5 and 6.

Figure 6:
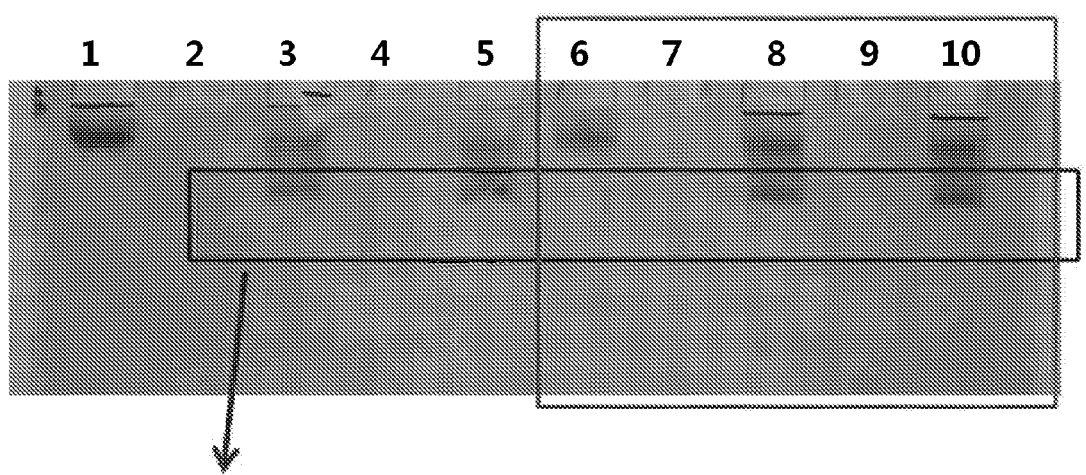
FIG. 6 shows the ability of aptamers of SEQ ID NOS: 1 and 2 to bind to pvLDH (*plasmodium vivax* lactate dehydrogenase) and pfLDH (*plasmodium falciparum* lactate dehydrogenase) as measured by EMSA (Electrophoretic mobility shift assay) (stained with coomassie blue, lane 1: PvLDH, lane 2: Aptamer #2, lane 3: Aptamer #2+PvLDH, lane 4.

The specification run in each lane of FIGS. 5 and 6 is summarized in Table 2, below. As shown in FIGS. 5 and 6, the aptamers of SEQ ID NOS: 1 and 2, although excavated through pvLDH, were found to bind to pfLDH as well as pvLDH, which was, in our opinion, attributed to the fact that pvLDH and pfLDH are very similar in function and structure due to a conservation rate of 90% or higher of the amino acid sequences therebetween.

TABLE 2

| 1 | PvLDH |
|---|---|
| 2 | Aptamer #2 |
| 3 | Aptamer #2 + PvLDH |
| 4 | Aptamer #1 |
| 5 | Aptamer #1 + PvLDH |
| 6 | PfLDH |
| 7 | Aptamer #2 |
| 8 | Aptamer #2 + PfLDH |

TABLE 2-continued

| | |
|---|---|
| 9 | Aptamer #1 |
| 10 | Aptamer #1 + PfLDH |

Example 6

Fluorescence Assay for Binding Strength Between pLDH and Aptamer

A mixture of 16 μg of pvLDH and 10 μL of magnetic beads was incubated for one hour in 100 μL of binding buffer (20 mM Tris, 50 mM NaCl, 5 mM KCl, 5 mM MgCl2, pH 8.0), followed by washing twice with the binding buffer to remove unbound pvLDH. Then, the beads were incubated for one hour with various concentrations of FAM-labeled aptamers. The aptamers which were not reacted with pvLDH were removed by washing.

Only the FAM-labeled ssDNA aptamer which was bound to pvLDH immobilized to the magnetic beads was separated using a magnet and quantitatively analyzed by fluorescence assay (1420 Victor multilabel counter, PerkinElmer, USA). As a result, Kd values of the DNA aptamers of SEQ ID NOS: 1 and 2 were measured. Kd values were also determined for pfLDH in the same manner. The results are given in Table 3, below.

TABLE 3

| Aptamer | Kd for pvLDH | Kd for pfLDH |
|---|---|---|
| SEQ ID NO: 1 | 16.8 nM | 38.7 nM |
| SEQ ID NO: 2 | 31.7 nM | 49.6 nM |

Example 7

Assay of Aptamer Mutant for Ability to Bind to pLDH

The aptamers excavated in Example 4 have the base sequences of SEQ ID NOS: 1 and 2, respectively, showing secondary structures of FIG. 4. The secondary structures of aptamers of SEQ ID NOS: 1 and 2 may be divided into three regions. FIG. 7 shows the secondary structures of the aptamer of SEQ ID NO: 1.

As shown in FIG. 7, the three regions (i) Loop 1, (ii) G-C rich stem, and (iii) Loop 2 are common to all the base sequences of the DNA aptamers specifically binding to pLDH. Each sequence is essential to binding to proteins.

EMSA (Electrophoretic mobility shift assay) was also performed to examine whether mutants derived from the aptamer of SEQ ID NO: 1 can bind to pvLDH.

The mutants of the aptamer of SEQ ID NO: 1 have the sequences of SEQ ID NOS: 3 to 5, respectively and are given in FIG. 8. EXSA results are shown in FIG. 9 and specifications for each lane in FIG. 9 are summarized in Table 4, below.

TABLE 4

| | |
|---|---|
| 1 | PvLDH |
| 2, 3 | aptamer, aptamer + PvLDH |
| 4, 5 | loop 1, loop 1 + PvLDH |
| 6, 7 | stem, stem + PvLDH |
| 8, 9 | loop 2, loop 2 + PvLDH |

As can be shown in FIGS. 8 and 9, the sequences modified at Loop 1 and Loop 2 did not bind to pvLDH protein at all, indicating that Loop 1 and Loop 2 are directly responsible for the binding of the protein to the aptamers. The G-C rich stem was partially modified because the significant modification thereof may destroy the secondary structure. As shown in FIG. 9, the binding strength was greatly reduced. Thus, the G-C rich stem was observed to be involved in the binding of the protein to the DNA aptamer in addition to contributing to the stable secondary structure of the DNA aptamer.

Therefore, the three regions are essential for the binding of the DNA aptamer, which means that even if sequences other than the three essential regions may be randomly mutated, the binding specificity is not altered.

It is understood to a person skilled in the art that the above description of the present invention is susceptible to various modifications, changes and adaptations, and the same are intended to be comprehended within the meaning and range of equivalents of the appended claims. Therefore, the embodiments and attached drawings disclosed in the present invention are not intended to limit the technical spirit of the present invention, but are intended to describe the invention. The technical spirit of the present invention is not limited to such embodiments and drawings.

What is claimed is:

1. A DNA aptamer specifically binding to pLDH (plasmodium lactate dehydrogenase), wherein the DNA aptamer comprises a base sequence having a homology of 70% or higher with SEQ ID NO: 1 or 2.

2. A composition for diagnosis of malaria comprising the DNA aptamer of claim 1.

3. A diagnostic kit of malaria using comprising the DNA aptamer of claim 1.

4. A method of diagnosis of malaria, the method comprising:

providing the DNA aptamer of claim 1;

contacting the DNA aptamer with a sample comprising pLDH (plasmodium lactate dehydrogenase) selected from the group consisting of pvLDH (plasmodium vivax lactate dehydrogenase), pfLDH (plasmodium falciparum lactate dehydrogenase), pmLDH (plasmodium malariae lactate dehydrogenase), poLDH (plasmodium ovale lactate dehydrogenase) and a combination thereof; and detecting a complex of the DNA aptamer and pLDH.

* * * * *

SEQUENCE LISTING

```
<160> NUMBER OF SEQ ID NOS: 11

<210> SEQ ID NO 1
<211> LENGTH: 36
<212> TYPE: DNA
<213> ORGANISM: Artificial Sequence
<220> FEATURE:
<223> OTHER INFORMATION: DNA specifically binding to pLDH

<400> SEQUENCE: 1
gttcgattgg attgtgccgg aagtgctggc tcgaac                             36

<210> SEQ ID NO 2
<211> LENGTH: 38
<212> TYPE: DNA
<213> ORGANISM: Artificial Sequence
<220> FEATURE:
<223> OTHER INFORMATION: DNA specifically binding to pLDH
```

```
<400> SEQUENCE: 2
gaactcattg gctggaggcg gcagtaccgc ttgagttc                                38

<210> SEQ ID NO 3
<211> LENGTH: 36
<212> TYPE: DNA
<213> ORGANISM: Artificial Sequence
<220> FEATURE:
<223> OTHER INFORMATION: DNA sequence of loop 1 mutation

<400> SEQUENCE: 3
gttcgaccaa attgtgccgg aagtgctggc tcgaac                                 36

<210> SEQ ID NO 4
<211> LENGTH: 36
<212> TYPE: DNA
<213> ORGANISM: Artificial Sequence
<220> FEATURE:
<223> OTHER INFORMATION: DNA sequence of G-C rich stem mutation

<400> SEQUENCE: 4
gttcgattgg attgtactga aagtgtcagt tcgaac                                 36

<210> SEQ ID NO 5
<211> LENGTH: 36
<212> TYPE: DNA
<213> ORGANISM: Artificial Sequence
<220> FEATURE:
<223> OTHER INFORMATION: DNA sequence of loop 2 mutaion

<400> SEQUENCE: 5
gttcgattgg attgtgccgg agacgctggc tcgaac                                 36

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
cccggatcca tgacgccgaa aattgt                                            26

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
cccctcgagt taaatgagcg ccttcatcct tttagtct                               38

<210> SEQ ID NO 8
<211> LENGTH: 90
<212> TYPE: DNA
<213> ORGANISM: Artificial Sequence
<220> FEATURE:
<221> NAME/KEY: MISC_FEATURE
<222> LOCATION: (32)..(71)
<223> OTHER INFORMATION: n= a, t, g, or c
<220> FEATURE:
<223> OTHER INFORMATION: Primer

<400> SEQUENCE: 8
cacctaatac gactcactat agcggatccg annnnnnnnn nnnnnnnnnn nnnnnnnnnn       60
```

```
-continued nnnnnnnnnn nctggctcga acaagcttgc                                    90

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
cacctaatac gactcactat agcgga                                        26

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
gcaagcttgt tcgagccag                                                19

<210> SEQ ID NO 11
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)
<223> OTHER INFORMATION: n is biotin-conjugated g

<400> SEQUENCE: 11
ncaagcttgt tcgagccag                                                19
```